United States Patent [19]

Nagai et al.

[11] Patent Number: 5,015,099

[45] Date of Patent: May 14, 1991

[54] DIFFERENTIAL ABSORPTION LASER RADAR GAS DETECTION APPARATUS HAVING TUNABLE WAVELENGTH SINGLE MODE SEMICONDUCTOR LASER SOURCE

[75] Inventors: Haruo Nagai, Isehara; Kiyoji Uehara, Tokyo; Masafumi Aizawa, Yamato, all of Japan

[73] Assignee: Anritsu Corporation, Tokyo, Japan

[21] Appl. No.: 492,784

[22] Filed: Mar. 12, 1990

[30] Foreign Application Priority Data

Mar. 23, 1989 [JP] Japan .................................. 1-71492
Dec. 29, 1989 [JP] Japan ................................. 1-343580

[51] Int. Cl.$^5$ ................................................ G01N 21/00
[52] U.S. Cl. .................................... 356/437; 250/339; 372/20; 372/31
[58] Field of Search ............................. 372/20, 31, 32; 356/437, 438; 250/205, 339, 343, 575

[56] References Cited

U.S. PATENT DOCUMENTS 4,567,366  1/1986  Shinohara ........................... 250/339
4,920,542  4/1990  Brosson et al. ........................ 372/20

FOREIGN PATENT DOCUMENTS 61-222289  10/1986  Japan .
62-98235    5/1987  Japan .
62-290190  12/1987  Japan .
1-254841   10/1989  Japan .
1-307639   12/1989  Japan .
1-307640   12/1989  Japan .

OTHER PUBLICATIONS

Applied Physics B, B38, 37–40 (1985), "Alternate Intensity Modulation of a Dual-Wavelength He—Ne Laser for Differential Absorption Measurements", K. Uehara.

Primary Examiner—James W. Davie
Attorney, Agent, or Firm—Frishauf, Holtz, Goodman & Woodward

[57] ABSTRACT

A light source has a tunable wavelength single mode semiconductor laser. The laser outputs a single mode laser beam having a wavelength tuned in accordance with a drive current and emits, for an object to be detected, at least a first laser beam having a first wavelength which is absorbed by a gas to be detected and a second laser beam having a second wavelength which is not absorbed by the gas to be detected. A controller switches the drive current having a predetermined value corresponding to the first or second wavelength at a predetermined period and supplies the drive current to the laser and controls the drive current having the predetermined value corresponding to the first or second wavelengths so that the first or second laser beams are alternately output from the laser with substantially the same power while the first and second wavelengths are maintained. A light-receiving unit receives first and second response light components generated when the first and second laser beams emitted alternately from the laser are incident on the object to be detected and outputs electrical signals corresponding to received light amounts of the first and second response light components. A signal processor receives the electrical signals from the light-receiving unit and processes the presence/absence of gas detection in accordance with a difference between the received light amounts of the first and second response light components.

11 Claims, 11 Drawing Sheets

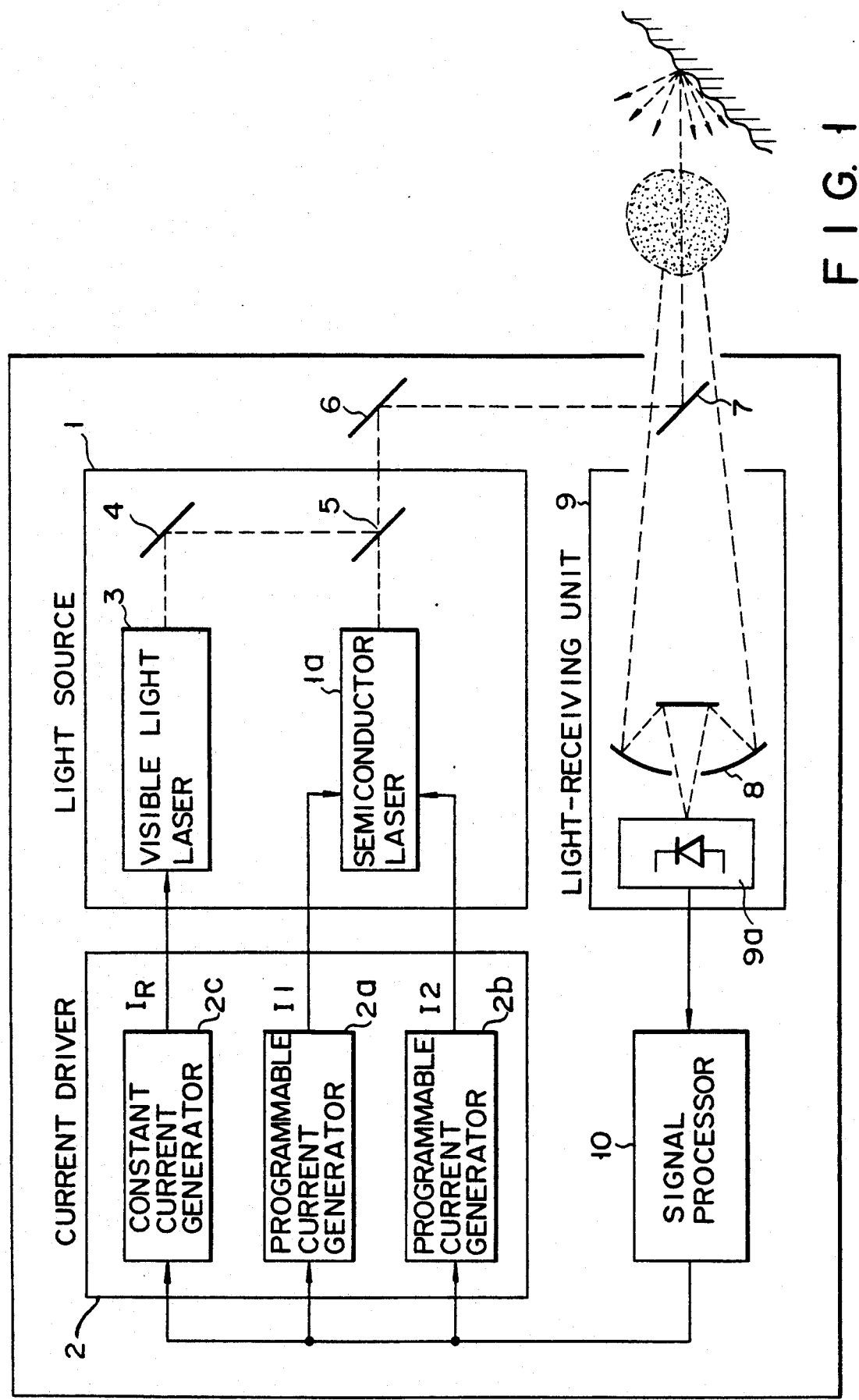
F I G. 1

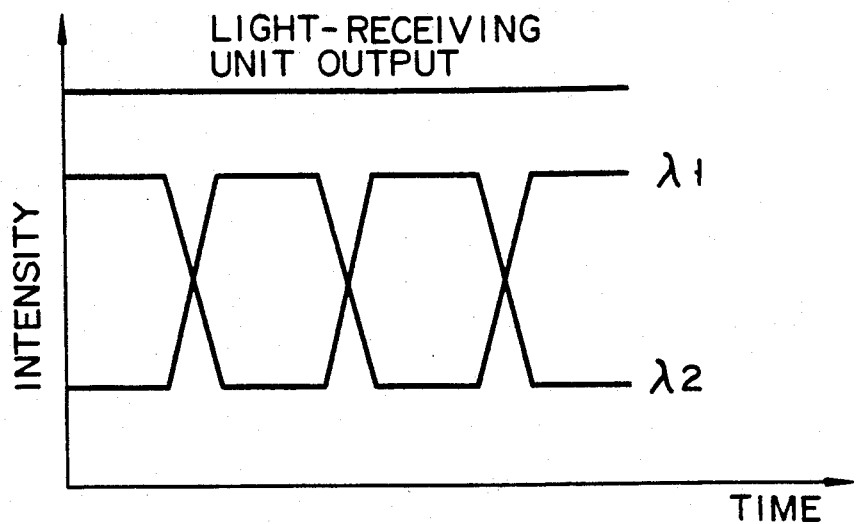
F I G. 2
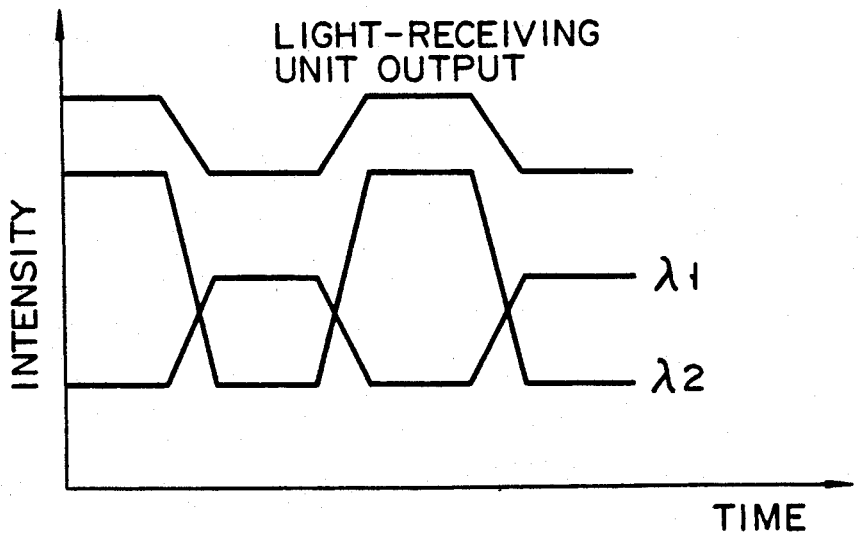
F I G. 3
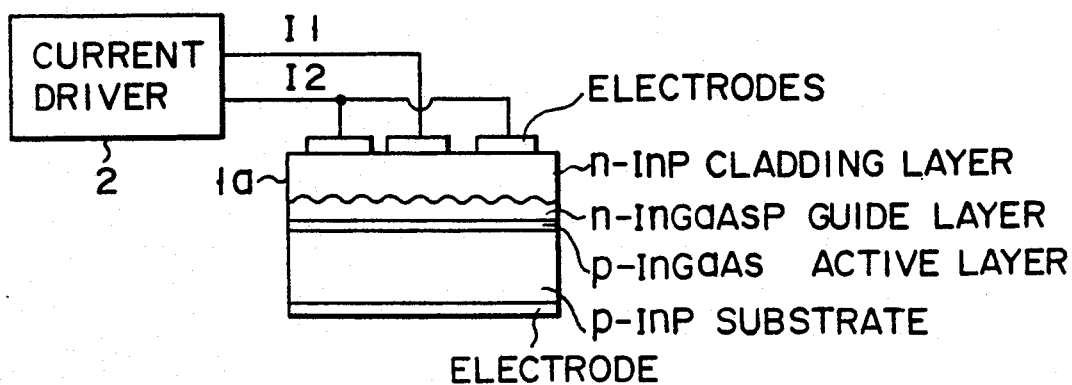
F I G. 4

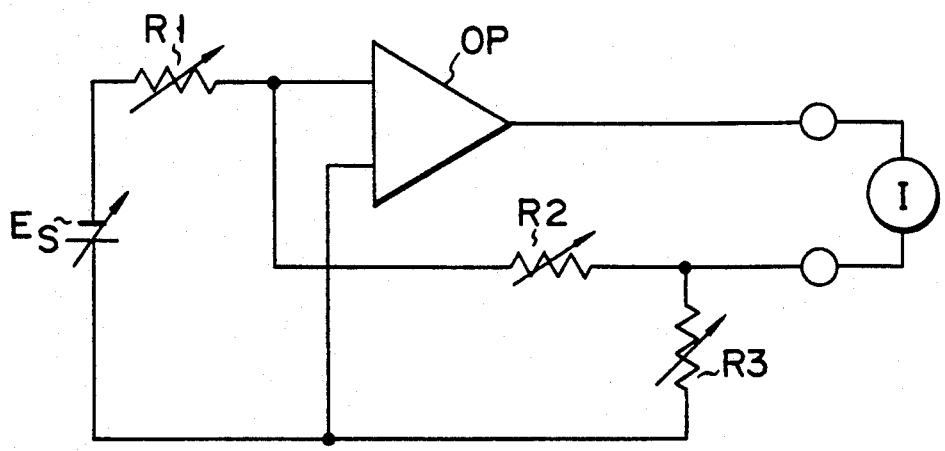
F I G. 6A
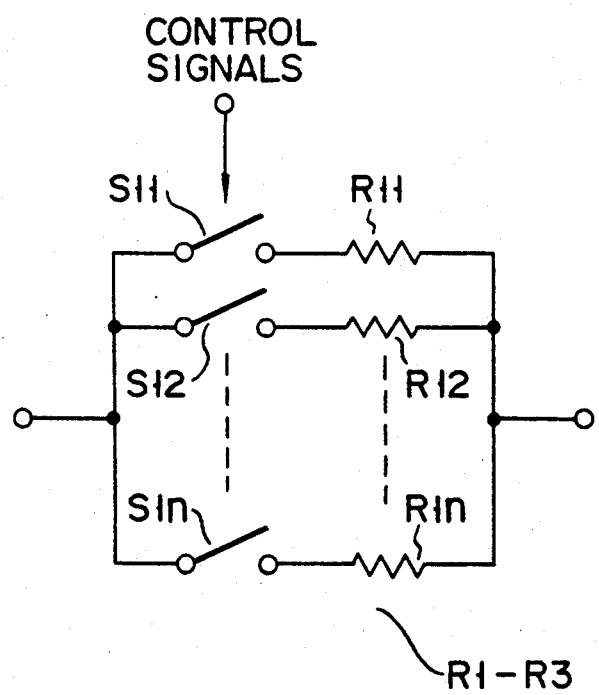
F I G. 6B

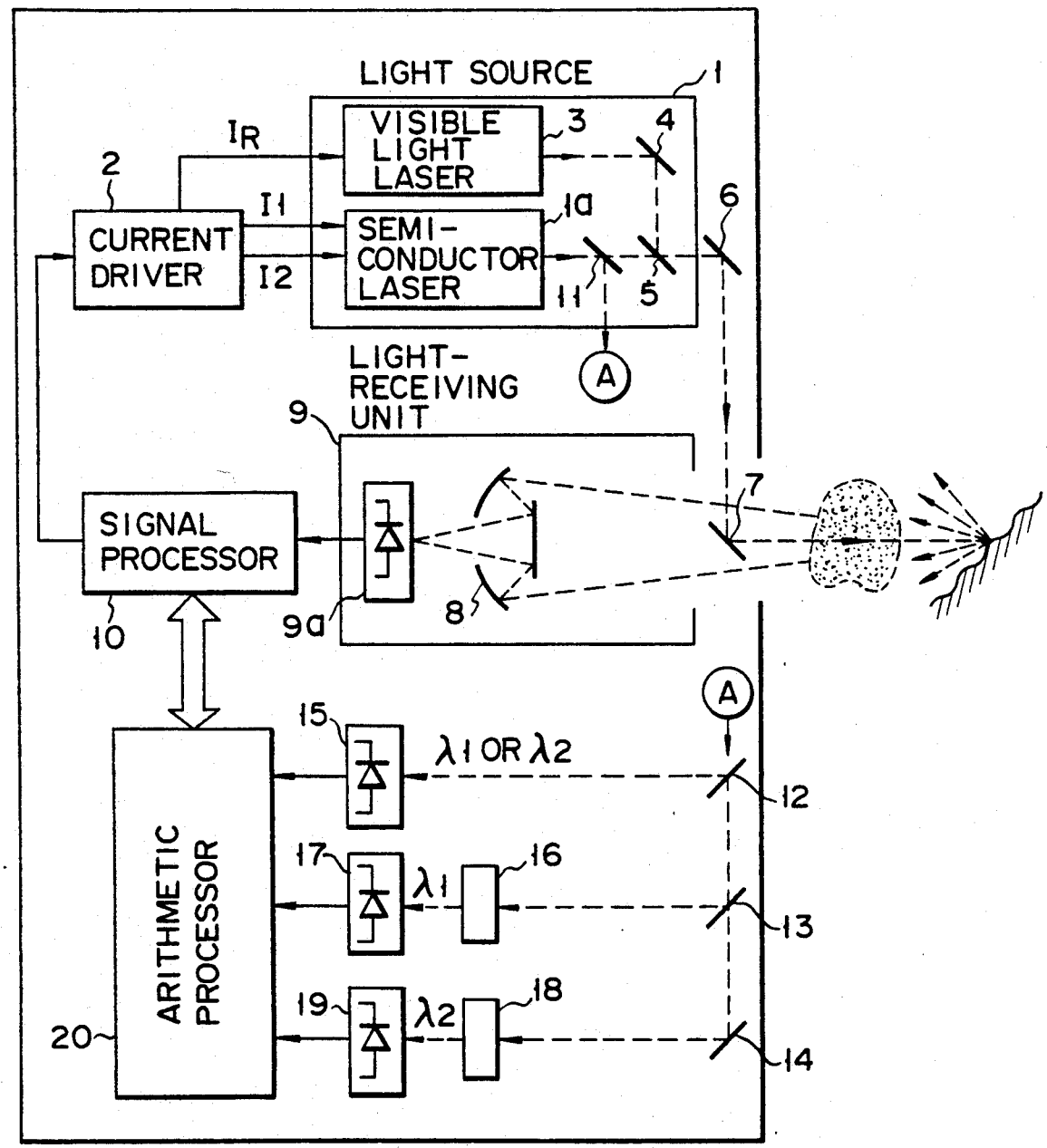
F I G. 13

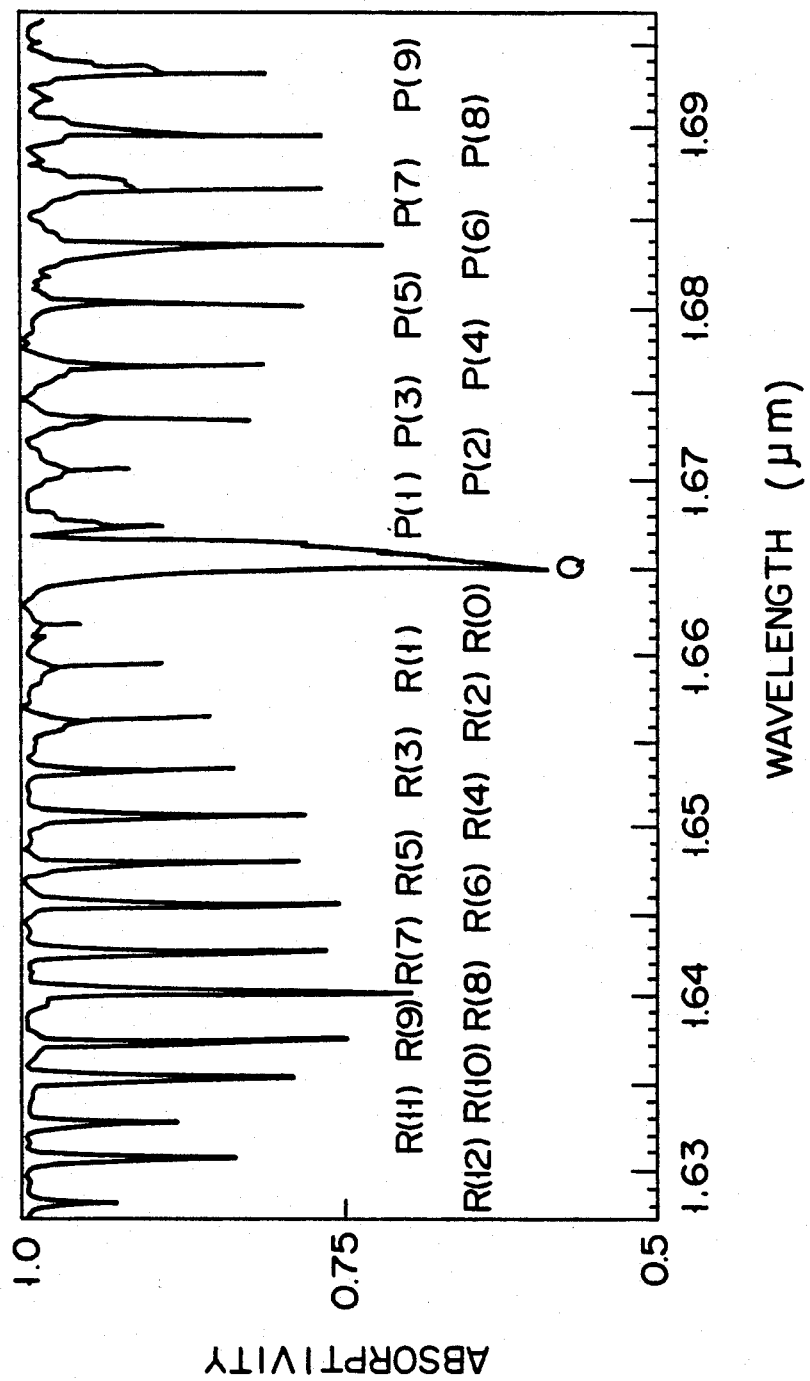

DIFFERENTIAL ABSORPTION LASER RADAR GAS DETECTION APPARATUS HAVING TUNABLE WAVELENGTH SINGLE MODE SEMICONDUCTOR LASER SOURCE

BACKGROUND OF THE INVENTION

1. Field of the Invention

The present invention generally relates to a differential absorption laser radar apparatus and, more particularly, to a gas detection apparatus for measuring an optical gas concentration by using absorption of light, thereby detecting a gas leakage of a city gas, a chemical plant or the like.

2. Description of the Related Art

A gas such as methane has an absorption band for light having a specific wavelength in accordance with rotation of molecules or vibrations between constituent atoms.

Detection of methane gas will be described below as an example. Methane has absorption bands at wavelengths of 1.33 $\mu$m 1.67 $\mu$m and 3.39 $\mu$m. By utilizing these absorption bands, various types of gas detection apparatuses using a differential absorption laser radar method have been proposed.

For example, a reference K. Uehara, "Alternate Intensity Modulation of a Dual-Wavelength He-Ne Laser for Differential Absorption Measurements", Appl. Phys. B 38, PP. 37 to 40 (1985) is known. This reference discloses as following. "A simple method is demonstrated for internal intensity modulation of the 3.391 and 3.392 $\mu$m emissions of a He-Ne laser with equal amplitudes and 180° out of phase to each other. A modulation amplitude of 0.7 mW peak-to-peak at 1 kHz for the individual emissions has been obtained from a laser plasma tube 50 cm long while maintaining the total-intensity modulation as low as 0.25/$\mu$W for a signal averaging time of 1 s. This light source can greatly implify the setup and improve the sensitivity of differential absorption measurements for the methane remote sensing."

Other known references are Published Unexamined Patent Application Ser. Nos. 61-222289 and 62-98235. According to techniques of gas detection apparatuses described in these references, an infrared He-Ne laser for outputting a laser beam having a wavelength of 3.3922 $\mu$m which is absorbed by methane and a laser beam having a wavelength of 3.3912 $\mu$m which is almost not absorbed by methane is used as a light source, laser beams having the above two wavelengths are alternately radiated in the air by an equal power, and direct light or reflected light of the radiated beams is received. If methane is present in the air, a difference is produced between reception light signal levels of the two wavelengths of 3.3922 $\mu$m and 3.3912/$\mu$m. That is, in the techniques described in these references, the presence of methane in the air (optical path) or its concentration are detected by measuring the difference.

According to techniques of a gas detection apparatus described in Published Unexamined Japanese Patent Application No. 62-290190, a semiconductor laser having an oscillation wavelength near 1.33 $\mu$m is used as a light source and modulated by two different current values having a predetermined current value as a center to oscillate at two wavelengths near 1.33 $\mu$m, thereby detecting methane as described above.

In the laser apparatus using the infrared He-Ne laser, however, a large number of parts such as a gas absorption cell and a mirror must be used. Therefore, an arrangement of the apparatus is complicated, and the apparatus is weak against mechanical vibrations. In addition, since a bulky driving system must be used, the apparatus becomes large and expensive.

In the two-wavelength laser apparatus using the semiconductor laser, when a current for driving a laser is changed to change the wavelength, an output value of a laser beam is simultaneously changed. Therefore, the apparatus cannot be directly used as a light source for a differential absorption laser radar method. For this reason, in order to substantially equalize the output values of the two wavelength components, a complicated output adjusting means comprising a gas absorption cell, a mirror and a photosensor is required. Therefore, in consideration of deterioration over time and the like, it is difficult to manufacture a gas detection apparatus with high precision and reliability.

SUMMARY OF THE INVENTION

It is, therefore, an object of the present invention to provide a new and improved differential absorption laser radar gas detection apparatus having tunable wavelength single mode semiconductor laser source which is strong against mechanical vibrations and can achieve high precision with a simple and compact arrangement.

According to one aspect of the present invention, there is provided a gas detection apparatus comprising:

light source means having a tunable wavelength single mode semiconductor laser, the tunable wavelength single mode semiconductor laser outputting a single mode laser beam having a wavelength tuned in accordance with a drive current and emitting, for an object to be detected, at least a first laser beam having a first wavelength which is absorbed by a gas to be detected or a second laser beam having a second wavelength which is not absorbed by the gas to be detected;

control means for switching the drive current having a predetermined value corresponding to the first or second wavelength at a predetermined period and supplying the drive current to the tunable wavelength single mode semiconductor laser, the control means controlling the drive current having the predetermined value corresponding to the first or second wavelength so that the first and second laser beams are alternately output from the tunable wavelength single mode semiconductor laser with substantially the same power while the first and second wavelengths are maintained;

light-receiving means for receiving first and second response light components generated when the first and second laser beams emitted alternately from the tunable wavelength single mode semiconductor laser are incident on the object to be detected and outputting electrical signals corresponding to received light amounts of the first and second response light components; and signal processing means for receiving the electrical signals from the light-receiving means and processing the presence/absence of gas detection in accordance with a difference between the received light amounts of the first and second response light components.

According to another aspect of the present invention, there is provided a gas detection apparatus comprising:

light source means having a tunable wavelength single mode semiconductor laser, the tunable wavelength single mode semiconductor laser outputting a single mode laser beam having a wavelength tuned in accordance with a drive current and emitting, for an object to be detected, at least a first laser beam having a first wavelength which is absorbed by a gas to be detected or a second laser beam having a second wavelength which is not absorbed by the gas to be detected;

first control means for switching the drive current having a predetermined value corresponding to the first or second wavelength at a predetermined period and supplying the drive current to the tunable wavelength single mode semiconductor laser, the first control means controlling the drive current having the predetermined value corresponding to the first or second wavelength so that the first and second laser beams are alternately output from the tunable wavelength single mode semiconductor laser with substantially the same power while the first and second wavelengths are maintained;

first light-receiving mean for receiving first and second response light components generated when the first and second laser beams emitted alternately from the tunable wavelength single mode semiconductor laser are incident on the object to be detected and outputting electrical signals corresponding to received light amounts of the first and second response light components;

signal processing means for receiving the electrical signals from the first light-receiving means and processing the presence/absence of gas detection in accordance with a difference between the received light amounts of the first and second response light components;

second light-receiving means for receiving the first and second laser beams emitted alternately from the tunable wavelength single mode semiconductor laser and outputting detection signals corresponding to the wavelengths and powers of the received first and second laser beams; and second control means for feeding back a correction signal for correcting the drive current having the predetermined value to the first control means in accordance with the detection signal from the second light-receiving means.

According to the gas detection apparatus of the first aspect having the above arrangement, the wavelengths and outputs of laser beams emitted alternately emitted from the semiconductor laser used as the light source can be independently controlled. Therefore, by flowing suitable laser drive currents corresponding to the two wavelengths, output components of the two wavelengths can be very easily equalized, and control precision of the wavelength and output can be increased.

According to the gas detection apparatus of the second aspect, in order to obtain desired values of a wavelength and an output level of the tunable wavelength single mode semiconductor laser, a feedback loop is formed to control the drive current of the tunable wavelength single mode semiconductor laser more effectively.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention:

FIG. 1 is a block diagram showing an arrangement of a system according to the first embodiment of the present invention;

FIG. 2 is a graph showing changes in two laser beams $\lambda_1$ and $\lambda_2$ and light-receiving portion outputs of the laser beams with respect to a time obtained when no methane is present in the air;

FIG. 3 is a graph showing changes in the two laser beams $\lambda_1$ and $\lambda_2$ and light-receiving portion outputs of the laser beams with respect to a time obtained when methane is present in the air;

FIG. 4 is a schematic view showing an arrangement of a 3-electrode DFB laser as a tunable wavelength single mode semiconductor laser used in the present invention;

FIG. 6A is a circuit diagram showing a detailed arrangement of a programmable current generator shown in FIG. 1;

FIG. 6B is a block diagram showing a detailed arrangement of a resistor switching circuit shown in FIG. 6A;

FIG. 13 is a block diagram showing an arrangement of a system according to the sixth embodiment of the present invention;

FIG. 15 is a graph showing light absorption characteristics of methane gas.

DETAILED DESCRIPTION OF THE PREFERRED EMBODIMENTS

Figure 5A:
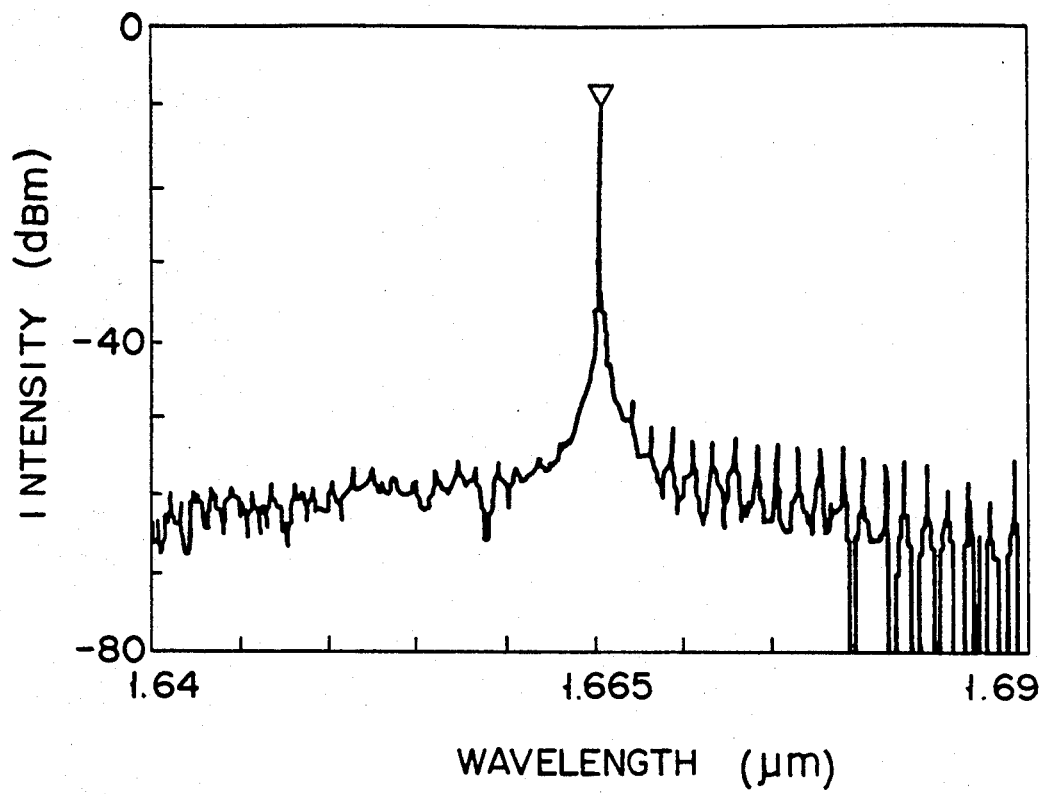
FIGS. 5A and 5B are graphs each showing a spectral distribution showing changes in a spectrum according to a distribution of an injection current to be flowed through the 3-electrode DFB laser shown in FIG. 4.

Reference will no be made in detail to the presently preferred embodiments of the invention as illustrated in the accompanying drawings, in which like reference characters designate like or corresponding parts throughout the several drawings.

(1st Embodiment)

First, the present invention will be briefly described below. The following three conditions are required for a two-wavelength laser used in a differential absorption laser radar method of this type:

(1) The optical axes of laser beams having two wavelengths must coincide with each other.

(2) The laser must be strong against mechanical vibrations.

(3) Wavelengths and intensities of two laser beams must be electrically controlled and their values must be independently modulated.

In order to satisfy the above requirements, in the gas detection apparatus of the present invention, a tunable wavelength single mode semiconductor laser is used as a light source to alternately output laser beams having two wavelengths. In order to set output levels of the laser beams having the two wavelengths to be predetermined values, the apparatus includes a controller for controlling injection currents to be flowed through electrodes of the tunable wavelength single mode semiconductor laser.

Note that 10 Å is sufficient as an interval between the two wavelengths and a modulation rate need only correspond to a frequency of about a few 10 kHz. These values can be satisfactorily realized by various types of tunable wavelength single mode semiconductor laser.

It is reported that an oscillation wavelength of a semiconductor laser operable at a temperature higher than room temperature currently falls within the range of a wavelength shorter than 1.7 μm and an absorption spectrum of methane has a strong peak in a wavelength range close to 1.67 μm. Therefore, the use of a tunable wavelength single mode semiconductor laser which oscillates in this wavelength range is suitable.

FIG. 1 is a block diagram showing a system arrangement of a gas detection apparatus according to an embodiment of the present invention, in which the tunable wavelength single mode semiconductor laser to be used as a light source is constituted by an InGaAs/InP-based 3-electrode DFB (Distributed Feedback) semiconductor laser which oscillates at a wavelength close to 1.67 μm.

In accordance with drive currents $I_1$ and $I_2$ alternately output at a predetermined period from first and second programmable current generators 2a and 2b, respectively, of a current driving unit 2 (to be described later), a tunable wavelength single mode semiconductor laser 1a (3-electrode DFB laser) of a light source unit 1 alternately emits with an equal intensity two laser beams having a wavelength $\lambda_1$ (in the first embodiment, 1.665/μm) which can be easily absorbed by methane and a wavelength $\lambda_2$ (in the first embodiment, 1.664 μm) which is not easily absorbed by methane.

A visible light laser (e.g., a red light laser) 3 of the light source unit 1 is driven by a constant current output from a constant current generator 2c of the current driving unit 2 to emit a guiding visible laser beam for indicating an emission direction of a laser beam from the semiconductor laser 1a. The laser beams emitted from the lasers 1a and 3 are synthesized by a mirror 4 and a half mirror 5 and radiated in the air by mirrors 6 and 7. The laser beams having the wavelengths $\lambda_1$ and $\lambda_2$ radiated in the air are scattered by roads, walls and the like. The scattered and returned laser beams are focused by a Cassegrain focusing mirror 8 of a light-receiving unit 9. A light signal of the focused light is converted into an electrical signal by a light-receiving element 9a, and the level of the electrical signal is detected by a signal processor 10 (to be described later), thereby detecting whether methane is present in the air.

Note that in order to stabilize the operation, control for temperature stabilization is performed for the light source unit 1, especially the laser element therein so as to hold a predetermined temperature.

This methane detection will be briefly described below with reference to FIGS. 2 and 3. Since the two laser beams $\lambda_1$ and $\lambda_2$ have very close wavelengths, they have substantially the same optical characteristics except for methane absorption characteristic. Therefore, if no methane is present in the air (optical path), the two laser beams alternately return with the same intensity as shown in FIG. 2. Since the two wavelengths cannot be identified from each other, a total light amount received by the light-receiving element 9a becomes constant, and its light-receiving unit output has no modulated frequency component. Therefore, even if the light-receiving unit output is lock-in-detected by the signal processor 10 in synchronism with a period for changing $I_1$ and $I_2$ in the current driving unit 2, the obtained output is zero.

If methane is present in the air (optical path), since only the laser beam $\lambda_1$ is absorbed and attenuated, a modulated component appears in the total light amount as shown in FIG. 3. Therefore, if the light-receiving unit output is lock-in-detected by the signal processor 10 in synchronism with the period for changing $I_1$ and $I_2$ in the current driving unit 2, a level corresponding to a difference between received beam amounts of the beams having the wavelengths $\lambda_1$ and $\lambda_2$ is output. The concentration of methane present in the air can be detected by this level.

An operation principle of the 3-electrode DFB laser used as the tunable wavelength single mode semiconductor laser 1a in the present invention will be described below.

Figure 5B:
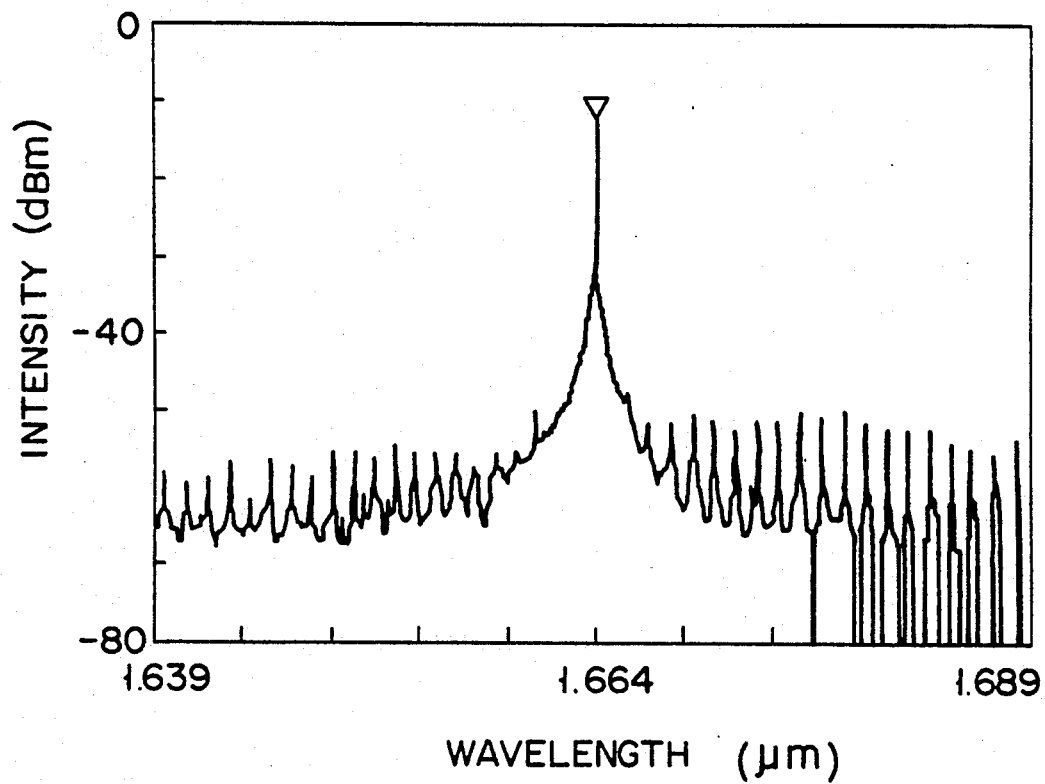

As shown in FIG. 4, the tunable wavelength single mode laser 1a obtained by forming an active layer, a guide layer and a cladding layer on a semiconductor substrate is connected to the current driving unit 2 so that drive currents $I_1$ and $I_2$ are supplied to its three electrodes. As shown in FIGS. 5A and 5B, under the control for temperature stabilization, an oscillation wavelength of the laser 1 is determined by a ratio of the drive current $I_1$ to the drive current $I_2$. By controlling the ratio to be a suitable value n or m, the laser 1 can be caused to oscillate at desired wavelengths $\lambda_1$ (μm) and $\lambda_2$ (μm). An output level of the laser beam from the laser 1 is determined by an injection current N represented by the sum $(I_1+I_2)$ of the drive currents.

That is, $I_2=nI_1$ is set to set the wavelength $\lambda_1$, $I_2=-mI_1$ is set to set the wavelength $\lambda_2$, and $I_1+I_2=N$ is set to set the output levels of the laser beams having the wavelengths $\lambda_1$ and $\lambda_2$ to be predetermined values.

The values n, m and N are slightly different for individual tunable wavelength single mode semiconductor lasers. The values n, m and N used in the 3-electrode DFB laser used in this embodiment are shown in Table 1 below.

TABLE 1

| Light Output | N | n | m |
|---|---|---|---|
| 1 mW | 45 mA | 1.45 | 2.51 |
| 3 mW | 70 mA | 1.49 | 2.49 |
| 5 mW | 90 mA | 1.53 | 2.47 |

FIG. 6A shows a detailed arrangement of the programmable current generators 2a and 2b shown in FIG. 1. Referring to FIG. 6A, each of resistor switching circuits $R_1$, $R_2$ $R_3$ is composed of a plurality of resistors $R_{11}$ to $R_{1n}$ connected in series with a plurality of analog switches $S_{11}$ to $S_{1n}$ respectively, as shown in FIG. 6B. That is, by selecting the switches $S_{11}$ to $S_{1n}$ by a control signal in accordance with a predetermined program, this programmable current generator varies a current I output from a power source E= via the resistor switching circuits $R_1$, $R_2$ and $R_3$ and an operational amplifier OP and alternately supplies the drive currents $I_1$ and $I_2$ at a predetermined period.

Note that total 4 generators including each two generators shown in FIG. 6A may be used for the drive currents $I_1$ and $I_2$ and switched by a wavelength switching control signal.

Figure 6C:
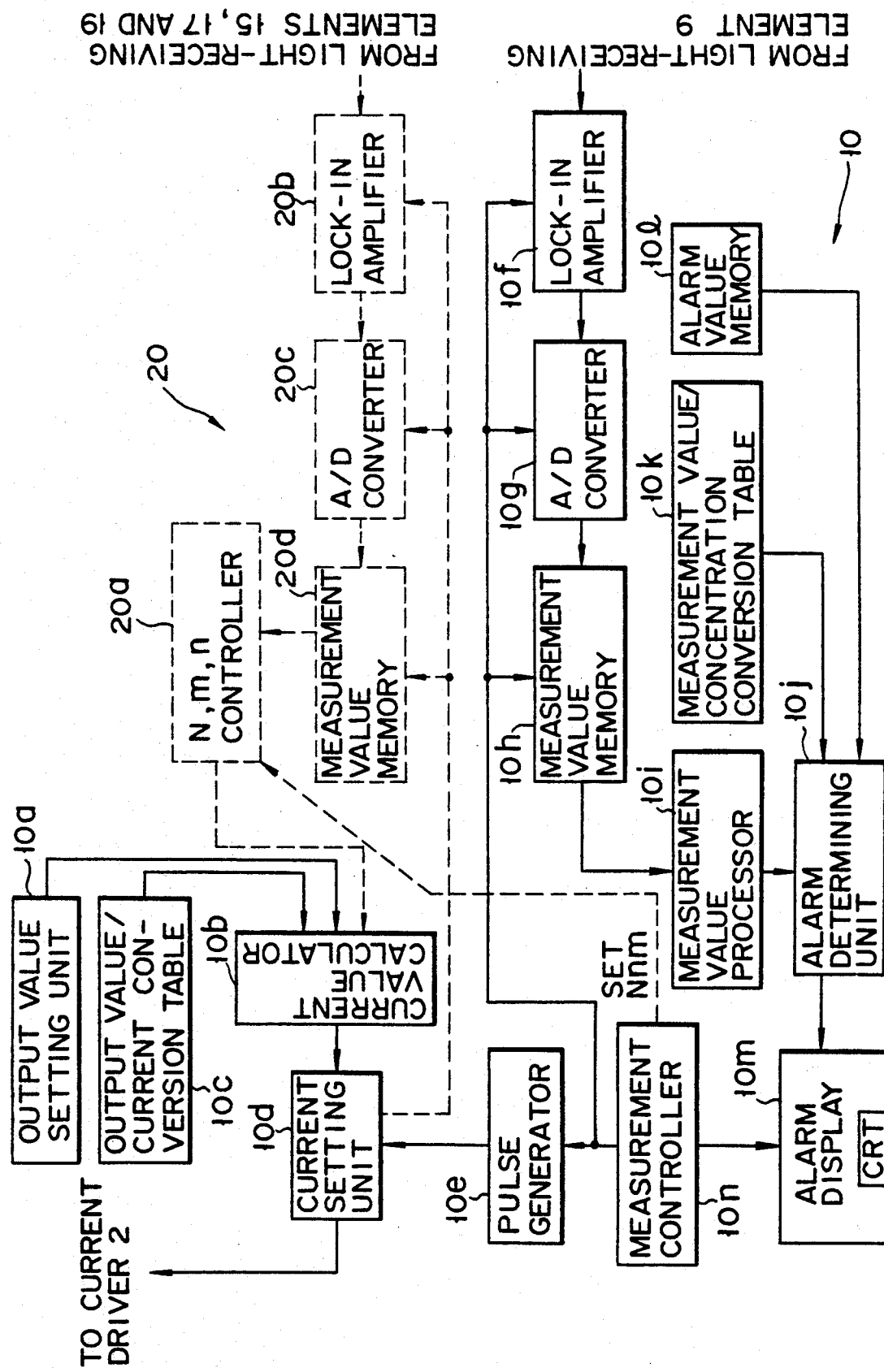
FIG. 6C is a block diagram showing in detail a signal processor shown in FIG. 1.

FIG. 6C shows a detailed arrangement of the signal processor 10 shown in FIG. 1. In order to operate the gas detection apparatus shown in FIG. 1, the signal processor 10 shown in FIG. 6C sets an output value capable of precisely controlling the temperature of the semiconductor laser with a high S/N ratio and without saturating the light-receiving element in accordance with a distance to a reflecting surface and the performance of the light-receiving element. An output value corresponding to a distance for the laser beam to reach the light-receiving element 9a of the light-receiving unit 9 is stored in an output value setting unit 10a. The output value is set by inputting this distance or manually inputting an output value.

A current value calculator 10b calculates $I_1$ and $I_2$ capable of obtaining the wavelengths $\lambda_1$ and $\lambda_2$ and a predetermined light output in accordance with the output value from the output value setting unit 10a with reference to an output value/current conversion table 10c.

A current setting unit 10d sets the values of $I_1$ and $I_2$ at the wavelengths $\lambda_1$ and $\lambda_2$ in the programmable current generators 2a and 2b, respectively, and outputs a switching signal for the wavelengths $\lambda_1$ and $\lambda_2$ in synchronism with a pulse signal from a pulse generator 10e. In addition, the current setting unit 10d starts an operation of the constant current generator 2c for generating a current $I_R$ to be supplied to the visible light laser 3.

Signals output from the light-receiving element 9a are converted into DC values by a lock-in amplifier 10f in synchronism with the wavelengths $\lambda_1$ and $\lambda_2$, the DC values are converted into digital values by an A/D converter 10g, and the digital values are stored in an area of a measurement value memory 10h corresponding to the number of generated pulses. A measurement value processor 10i performs averaging or correlation processing for the measurement values stored in the memory 10h, thereby calculating a difference between the measurement values at the wavelengths $\lambda_1$ and $\lambda_2$.

An alarm determining unit 10j determines a concentration with reference to an output from the measurement value processor 10i and a measurement value/concentration conversion table 10k. If the determined concentration is higher than an alarm value stored in an alarm value memory 10l, the alarm determining unit 10j outputs an alarm.

An alarm display 10m displays measurement items such as a concentration and an alarm in accordance with the output from the alarm determining unit 10j and measurement conditions output from a measurement controller 10n on a CRT.

Figure 7A:
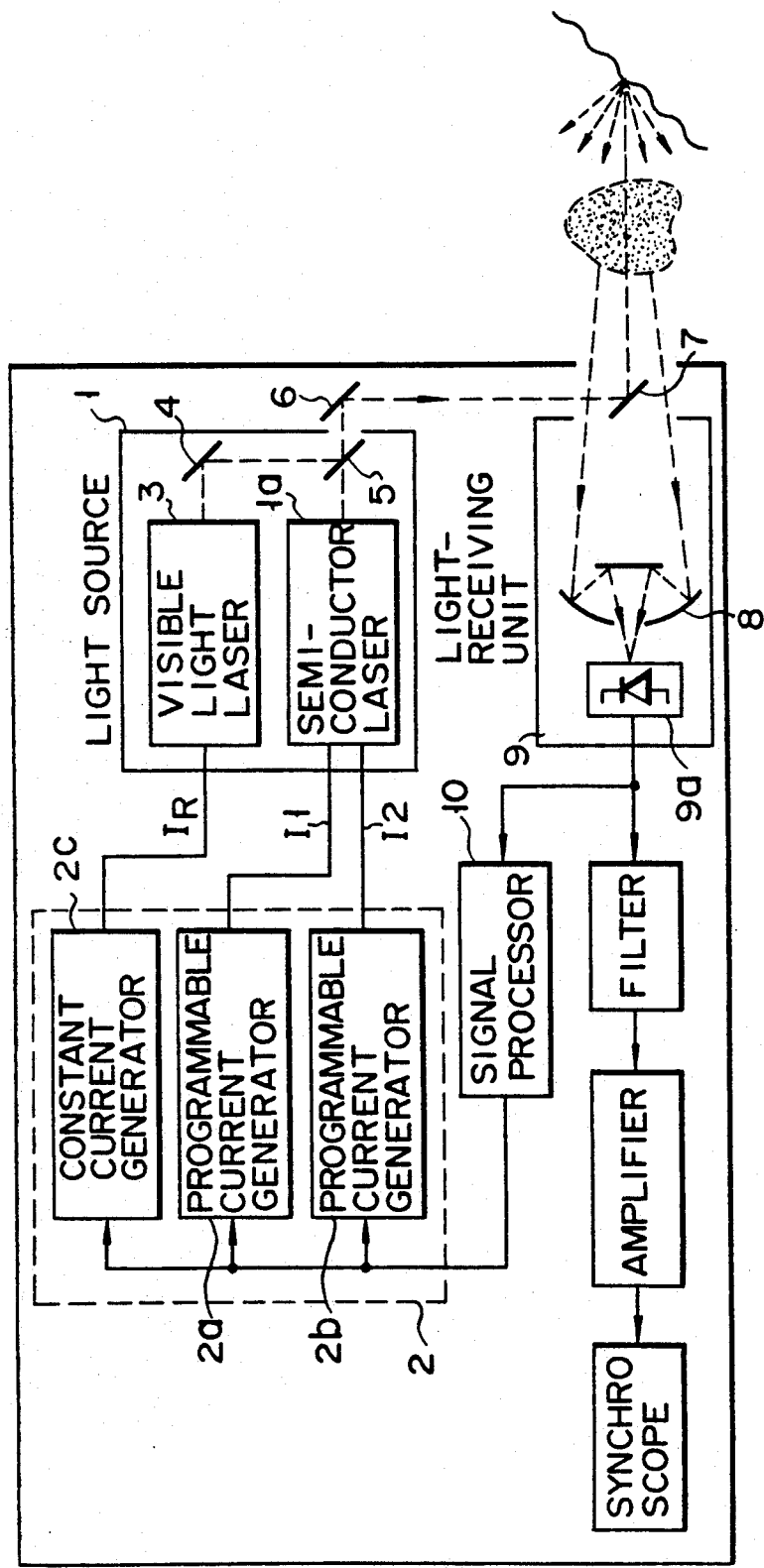
FIGS. 7A and 7B show a block diagram showing an arrangement for displaying the presence/absence of gas detection on the basis of an output from the gas detection apparatus shown in FIG. 1 and an example of the display.

FIG. 7A shows a system arrangement used to display the presence/absence of a detection gas on a synchroscope. The arrangement shown in FIG. 7A is the same as that shown in FIG. 1 except that an output from a light-receiving element 9a is supplied to a synchroscope 103 via a filter 101 and an amplifier 102.

In the arrangement shown in FIG. 7A, the concentration of a detected gas is observed on the synchroscope 103 as an amplitude of a wave having the same frequency (10 KHz) as a repeating frequency of pulses from programmable current generators 2a and 2b.

Figure 7B:
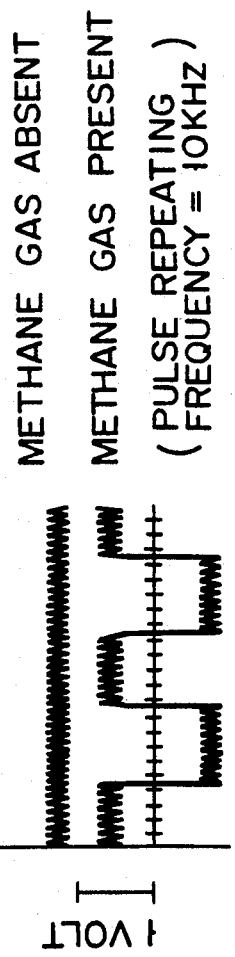

FIG. 7B shows a detailed display obtained when a gas cell (length = 10 cm) containing air containing 10% of methane gas is used as a sample and measurement is performed at the middle point between the apparatus and a flat wall (separated from the apparatus by 1 m) having high reflectivity. In this measurement, an output radiated on the wall was 1.5 mW, and the diameter of a light-receiving reflecting mirror was 15 cm.

As shown in FIG. 7B, the signal intensity of this gas detection system is sufficiently high, and even 0.01% of methane can be detected if the sensitivity of the synchroscope 103 is increased.

The second to sixth embodiments will be described below. In each of these embodiments, a system arrangement of a gas detection apparatus is the same as that of the first embodiment shown in FIG. 1 and therefore is not shown.

(2nd Embodiment)

Figure 8:
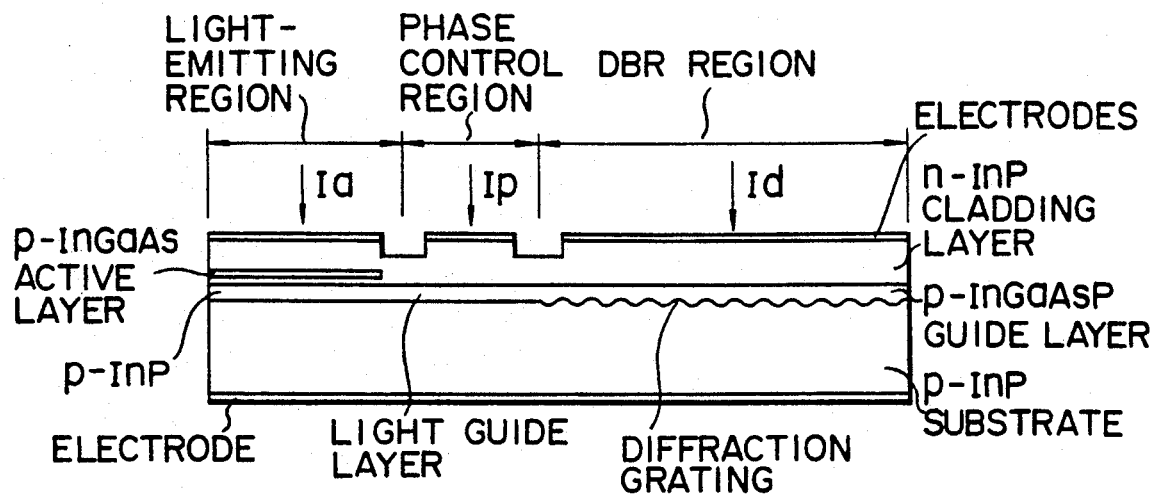
FIG. 8 is a sectional view showing a 3-electrode DBR laser as a tunable wavelength single mode semiconductor laser according to the second embodiment of the present invention.
Figure 9:
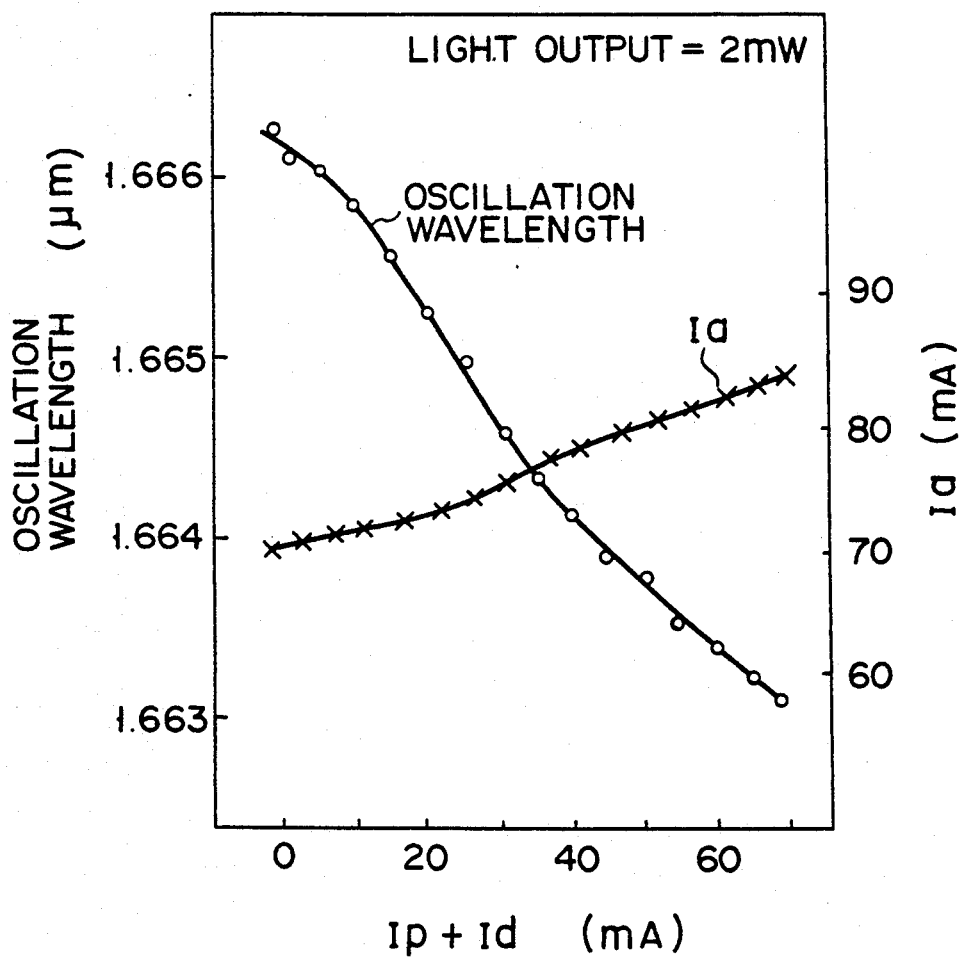
FIG. 9 is a graph showing characteristics of an oscillation wavelength of the 3-electrode DBR laser with respect to an applied current.

FIG. 8 shows an arrangement of a 3-electrode DBR (Distributed Bragg Reflector) laser used as a tunable wavelength single mode semiconductor laser 1a according to the second embodiment of the present invention, and FIG. 9 shows characteristics of an oscillation wavelength with respect to an applied current. In the laser shown in FIG. 8, currents to be injected in a light-emitting region, a phase control region and a DBR region are denoted by reference symbols Ia, Ip and Id, As shown in FIG. 9, a light output P is substantially determined by Ia to be injected in the light-emitting region. Since, however, the light output is changed when Ip and Id are changed, Ia to be injected in the light-emitting region is also changed. In addition, since the refractive index of a diffraction grating can be controlled by an electric field applied to the diffraction grating, the oscillation wavelength can be determined by a sum of Ip and Id to be injected in the phase control region and the DBR region. That is, Ip/(Ia+Ip+Id), Id/(Ia+Ip+Id) and Ia+Ip+Id are controlled to be desired values.

(3rd Embodiment)

Figure 10:
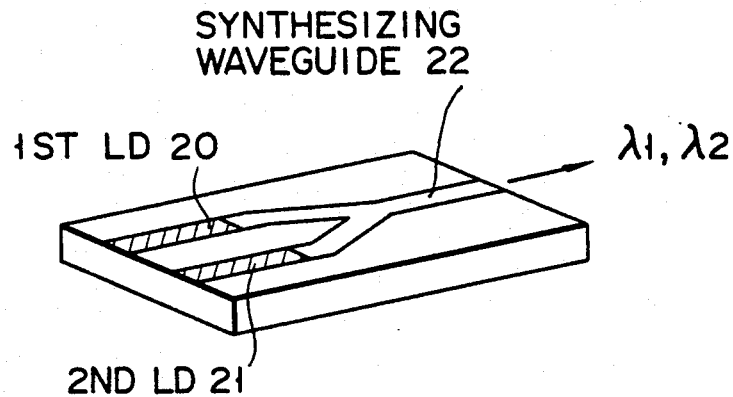
FIG. 10 is a perspective view showing an arrangement of an integrated element DFB laser according to the third embodiment of the present invention.

FIG. 10 shows an arrangement of an integrated DFB laser element used as a tunable wavelength single mode semiconductor laser 1a according to the third embodiment of the present invention. The 3-electrode DFB laser of this embodiment is obtained by integrating a first laser diode (to be referred to as an LD hereinafter) 20, a second LD 21 and a synthesizing waveguide 22. A laser beam emitted from the first LD 20 has a wavelength $\lambda_1$ (in the third embodiment, 1.665 μm) which is easily absorbed by methane, and a laser beam emitted from the second LD 21 has a wavelength $\lambda_2$ (in the third embodiment, 1.664 μm) which is not easily absorbed by methane. Currents applied to the first and second LDs 20 and 21 are alternately switched so that the wavelengths $\lambda_1$ and $\lambda_2$ are alternately emitted with equal intensity. Note that the wavelengths are switched and the output intensity is controlled in the same manner as in the first embodiment. It is a matter of course that a 3-electrode DBR laser can be used instead of the 3-electrode DFB laser in the third embodiment.

(4th Embodiment)

Figure 11:
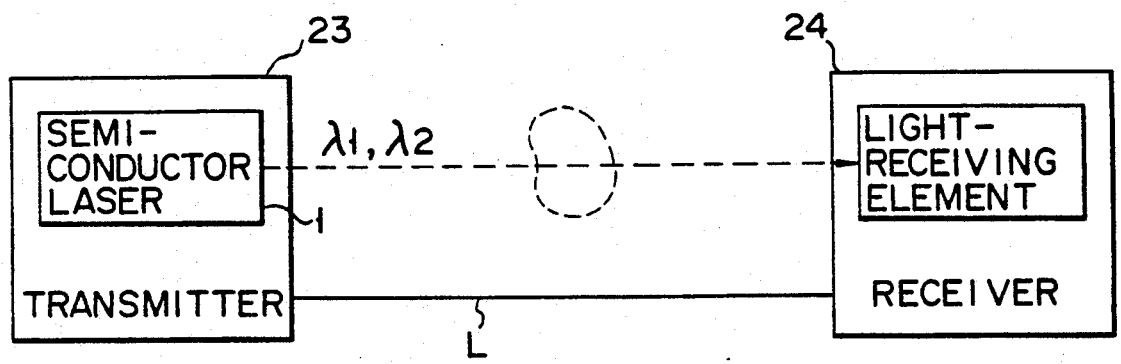
FIG. 11 is a block diagram showing an arrangement of a system according to the fourth embodiment of the present invention.

FIG. 11 shows a system arrangement according to the fourth embodiment of the present invention in which absorption of transmission light is used. In the first to third embodiments, reflected light is used to detect a gas present in the air.

In the fourth embodiment, however, light propagating in a space and transmitted through a gas to be detected is used. A light source of a transmitter 23 and a light-receiving unit and a signal processor of a receiver 24 have the same arrangements as those of the first, second or third embodiment. In order to synchronize the transmitter 23 and the receiver 24, a sync signal using a laser beam having a wavelength $\lambda_2$ (in the fourth embodiment, 1.664 $\mu$m) which is not easily absorbed by methane is transmitted from the transmitter 23 to the receiver 24. The receiver 24 receives the sync signal to establish synchronization and performs gas detection processing. The transmitter 23 also transmits a light output value, various parameters such as an alarm threshold value and data such as a control signal to the receiver 24 by using the laser beam having the wavelength $\lambda_2$.

Note that this data transmission can be performed by using another line L such as a metallic line without using the laser beam having the wavelength $\lambda_2$. In addition, data in the receiver 24 can be transmitted to the transmitter 23.

(5th Embodiment)

Figure 12:
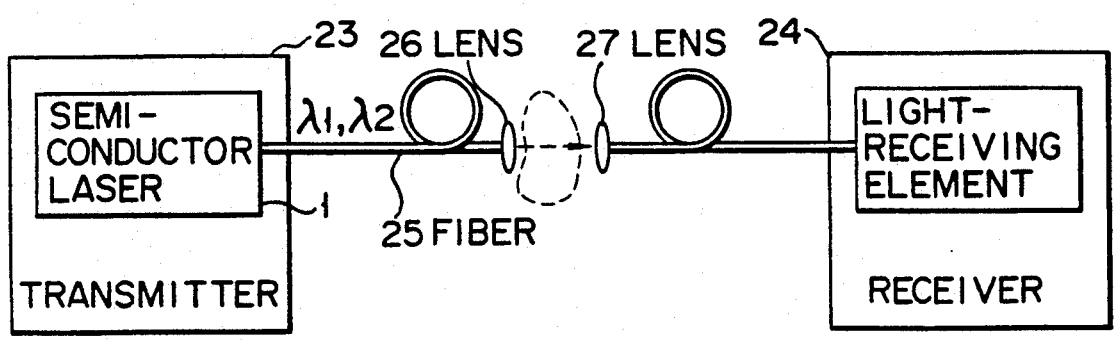
FIG. 12 is a block diagram showing an arrangement of a system according to the fifth embodiment of the present invention.

FIG. 12 shows a system arrangement according to the fifth embodiment of the present invention in which absorption of transmission light is used. The fifth embodiment can be used especially as a monitoring apparatus for a gas leakage in a pipe line in a chemical plant or the like. While light is emitted in a space in the fourth embodiment, it is emitted in a fiber 25 in the fifth embodiment. The system according to the fifth embodiment comprises a lens 26 for emitting light from the fiber 25 into a space at a plurality of portions of a pipe line (not shown), and a lens 27 for focusing the light emitted in the space and transmitted through a gas and supplying the focused light into the fiber 25. Since the fiber is used as a light transmission path, not only light propagating in an emission direction but also light reflected toward a transmitter 23 can be used. That is, by using a wavelength $\lambda_1$ (in the fifth embodiment, 1.665 $\mu$m) which is easily absorbed by methane as the wavelength of light emitted from the transmitter 23, a portion of methane leakage in a pipe line using methane can be detected.

(6th Embodiment)

First, the sixth embodiment will be briefly described below.

(1) An apparatus comprises a light-receiving unit for detecting the wavelength and the output level of a tunable wavelength single mode semiconductor laser. The light-receiving unit includes a discriminator for discriminating two wavelengths and a light-receiving element for detecting the discriminated output.

(2) The apparatus comprises an arithmetic processor for receiving a signal from the light-receiving unit and, in accordance with the received light level, calculating a total sum of currents to be flowed to a plurality of electrodes of the tunable wavelength single mode semiconductor laser and a ratio of the current to be flowed to each electrode to the total sum.

(3) The apparatus comprises a current driver for receiving a control signal from the arithmetic processor and controlling the current to be flowed to each electrode.

FIG. 13 shows a system arrangement of a gas detection apparatus according to the sixth embodiment of the present invention. In general, when a current is flowed to a semiconductor laser in order to cause the semiconductor laser to oscillate and emit a laser beam, the semiconductor laser itself generates heat. Therefore, even if the semiconductor laser is driven by a constant current under the temperature control of an element, it is difficult to maintain precision in the wavelength and intensity of a laser beam.

According to the sixth embodiment, in the arrangement of the first embodiment, the wavelengths ($\lambda_1$ and $\lambda_2$) and intensities of two laser beams are monitored, and a current output from a current driver 2 is controlled in accordance with the monitoring results, thereby improving precision in the wavelengths and intensities of the two laser beams alternately emitted from a semiconductor laser 1a (in the sixth embodiment, a 3-electrode DFB laser).

Half mirrors 12 and 13 and a mirror 14 are arranged such that a laser beam emitted from the semiconductor laser 1a is split by a half mirror 11 and the split laser beams are guided to light-receiving elements to be described below (as indicated by — in FIG. 13).

A laser beam split by the half mirror 12 is incident on a light-receiving element 15. An arithmetic processor 20 calculates the intensities of laser beams having wavelengths $\lambda_1$ and $\lambda_2$ in accordance with an output from the light-receiving element 15.

A laser beam split by the half mirror 1 is incident on a wavelength discriminator 16 for selectively splitting light having a wavelength of 1.665 $\mu$m and emitting an output to a light-receiving element 17. The arithmetic processor 20 calculates the intensity of the laser beam having the wavelength $\lambda_2$ in accordance with an output from the light-receiving element 17.

A laser beam reflected by the mirror 14 is incident on a wavelength discriminator 18 for selectively splitting light having a wavelength of 1.664 $\mu$m and emitting an output to a light-receiving element 19. The arithmetic processor 20 calculates the intensity of the laser beam having the wavelength $\lambda_2$ in accordance with an output from the light-receiving element 19.

Measurement (calculation) of the intensity and wavelength of each laser beam will be described in detail below.

(1) In order to control the wavelength $\lambda_1$ to be 1.665 $\mu$m, the arithmetic processor 20 scans n of $I_2 = nI_1$ in Table 1 around 1.45. An incident laser beam is selected by the wavelength discriminator 16, and n is controlled so that the discriminated signal intensity received by the light-receiving element 17 is maximized.

(2) In order to maintain the intensity of $\lambda_1$ to be 1 mW, the arithmetic processor 20 maintains n determined in item (1) constant and scans N of $I_1 + I_2 = N$ in Table 1 around 45 mA, thereby emitting a laser beam on the light-receiving element 15. N is controlled in accordance with an output from the element 15 so that the intensity of $\lambda_1$ is maintained to be 1 mW.

(3) In order to control the wavelength $\lambda_2$ to be 1.664 μm, the arithmetic processor 20 scans m of $I_2 = mI_1$ in Table 1 around 2.51. An incident laser beam is selected by the wavelength discriminator 18, and m is controlled so that the discriminated signal intensity received by the light-receiving element 19 is maximized.

(4) In order to maintain the intensity of $\lambda_2$ to be 1 mW, the arithmetic processor 20 maintains m determined in item (1) and scans N of $I_1 + I_2 = N$ in Table 1, and a laser beam is emitted onto the light-receiving element 15. N is controlled in accordance with an output from the light-receiving element 15 so that the intensity of $\lambda_1$ is maintained to be 1 mW.

By performing operations from items (1) to (4), the wavelengths and intensities of $\lambda_1$ and $\lambda_2$ can be maintained constant.

Figure 14:
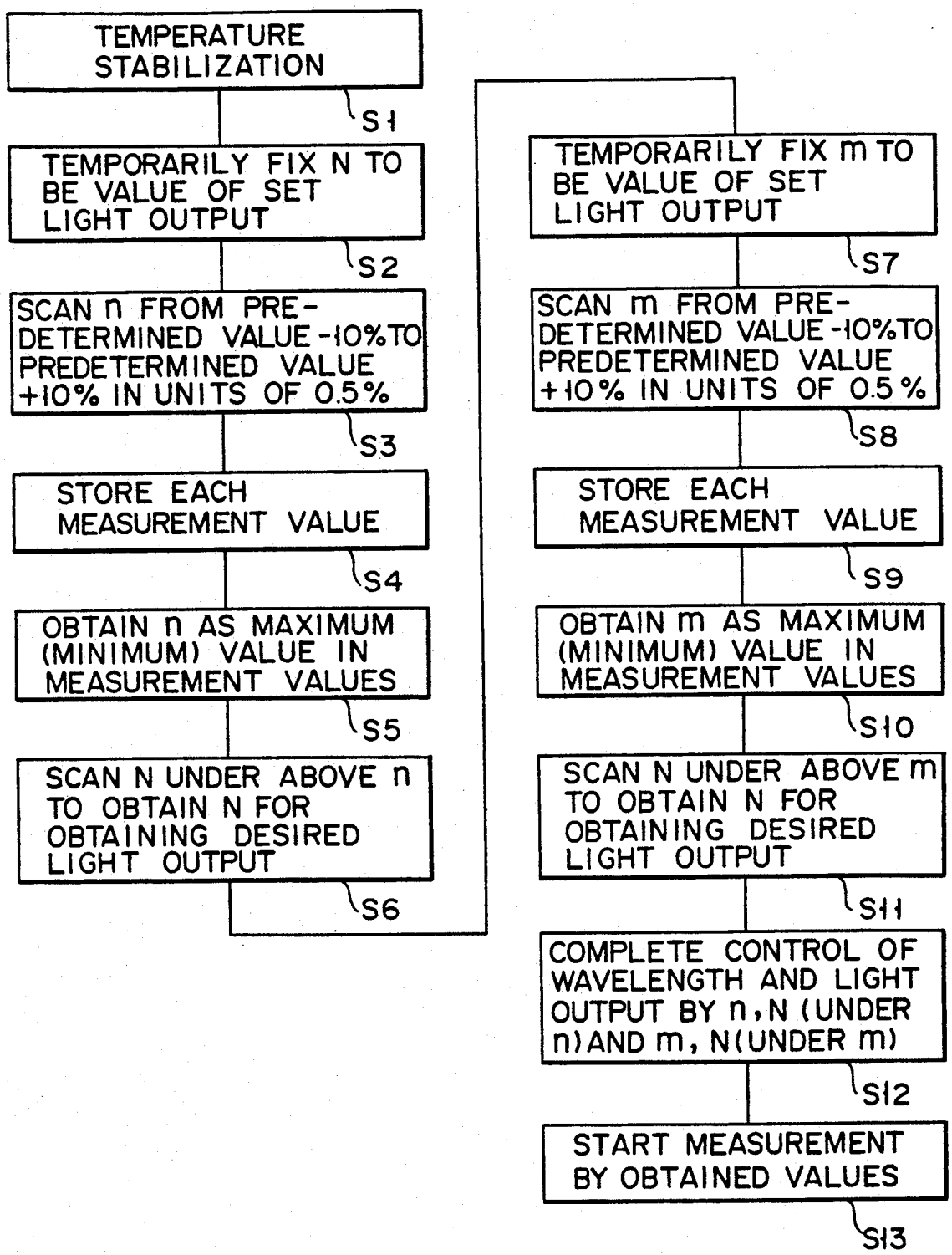
FIG. 14 is a flow chart for explaining an operation of the system shown in FIG. 13.

Processing according to the sixth embodiment performed before measurement is started will be described below with reference to FIG. 6C in which a detailed arrangement of the arithmetic processor 20 shown in FIG. 13 is indicated by a broken line and a flow chart including steps S1 to S13 shown in FIG. 14.

In step S1, the temperature of the light source unit 1 is stabilized. In order to start measurement, an Nnm set signal is output from a measurement controller 10n to an Nmn controller 20a to perform the following processing.

(a) First, Nn at $\lambda_1$ is determined.

In accordance with an output from the Nmn controller 20a, a current value calculator 10b temporarily fixes N to be a value of a set light output. Then, n is scanned from a predetermined value —10% to a predetermined value + 10% in units of 0.5 (steps S2 and S3).

A lock-in amplifier 20b converts a signal output from the light-receiving element 17 into a DC value in synchronism with an output from a current setting unit 10d. The DC value is converted into a digital value by an A/D converter 20c, and the digital value is stored in an area of a measurement value memory 20d corresponding to the value of n (step S4).

The Nmn controller 20a determines n corresponding to a maximum value of the digital values at the respective stored values of n (step S5).

Whether the output from the wavelength discriminator becomes the maximum or minimum value at $\lambda_1$ is determined in accordance with the type of wavelength discriminator. This is the same as in step S9 (to be described later) in which is replaced by $\lambda_2$.

The current value calculator 10b scans N under the value of n in accordance with the output from the Nmn controller 20a (step S6).

The lock-in amplifier 20b converts the signal output from the light-receiving element 15 into a DC value in synchronism with the output from the current setting unit 10d. The DC value is converted into a digital value by the A/D converter 20c, and the digital value is stored in an area of the measurement value memory 20d corresponding to the value of N.

The Nmn controller 20a determines N corresponding to a maximum value of the digital values at the respective stored values of N.

In this embodiment, since the wavelength discriminator is constituted by a bandpass filter, the maximum value of the digital values is determined. If, however, the wavelength discriminator is constituted by an absorption cell which maximally absorbs light at the light wavelength $\lambda_1$, the minimum value of the digital values is determined.

In this embodiment, n is finely scanned from a predetermine value — 10% to a predetermined value + 10% in units of 0.5. The processing, however, may be performed such that n is more discretely scanned to obtain measurement values and the value of n for obtaining a maximum value of the measurement values is calculated on the basis of the measurement values.

(b) Nm at $\lambda_2$ is determined (steps S7 to S12) The processing corresponding to $\lambda_2$ is the same as that described in item a) above except that n is replaced with m.

The above series of operations can be very easily performed under the highly precise temperature control. Even if the temperature of a gas detection apparatus including the tunable wavelength single mode semiconductor laser varies, a current to be applied to the laser can be controlled since the wavelength and the output can be independently controlled in the tunable wavelength single mode semiconductor laser. Therefore, it is obvious that an influence of temperature variation can be prevented to easily perform gas detection. This is a great advantage of the present invention.

According to the present invention having the above arrangement, a relationship between a methane concentration at specific intensities of laser beams having wavelengths $\lambda_1$ and $\lambda_2$ and an intensity of a laser beam incident on the light-receiving element 9 is stored beforehand in the signal processor 10. Therefore, a methane concentration in the air can be precisely measured.

Examples of the wavelength discriminator are a Fabry-Pérot interferometer and an absorption cell using absorption characteristics of a specific substance. Especially as a wavelength discriminator for $\lambda_1$, an absorption cell for methane to be detected can be used to perform simplest and most precise discrimination.

In each of the above embodiments, the 3-electrode DFB laser is described as an example of the tunable wavelength single mode semiconductor laser. A 2-electrode DFB laser may be used to achieve the same functions. In addition, the present invention can be similarly applied to a tunable wavelength DBR laser, an integrated DFB laser and an integrated DBR laser.

In each of the above embodiments, absorption near a wavelength of 1.665 μm is used. Since, however, a large number of absorption lines of methane are present near this wavelength as shown in FIG. 15, the used wavelength is not limited to 1.665 μm. In consideration of wavelength dependency of a practical light-receiving element, if 1.665 μm is used for both Ge and InGaAs, this wavelength is too long, and the sensitivity is reduced. If an InGaAs active layer is used in an InP/InGaAsP-based laser as a light source to oscillate near 1.665 μm the obtained output and temperature characteristics are inferior to those obtained by oscillation at a shorter wavelength. In consideration of these situations, by using an absorption peak at, e.g., 1.64 μm performance of the light source, the light-receiving element and the like can be further improved to execute detection of methane with higher sensitivity.

As has been described above, according to the gas detection apparatus of the present invention, the tunable wavelength single mode semiconductor laser is used to alternately output two laser beams. Therefore, since portions using a mechanical operation in a conventional apparatus are replaced with electrical signals, the number of movable portions is reduced to reduce the number of parts. As a result, the size of the apparatus is reduced and its reliability is improved.

The wavelength and output of the tunable wavelength single mode semiconductor laser of the present invention can be independently controlled. Therefore, a most effective wavelength corresponding to absorption characteristics of a gas to be detected can be used, and the laser can be easily controlled. As a result, control precision for the wavelength and output is increased to largely improve detection precision of various types of gases.

Additional embodiments of the present invention will be apparent to those skilled in the art from consideration of the specification and practice of the present invention disclosed herein. It is intended that the specification and examples be considered as exemplary only, with the true scope of the present invention being indicated by the following claims.

What is claimed is:

1. A gas detection apparatus, comprising:

light source means including a tunable wavelength single mode semiconductor laser, said tunable wavelength single mode semiconductor laser including means for outputting a single mode laser beam having a wavelength tuned in accordance with a drive current to a first optical path and a second optical path, and means for emitting, for an object to be detected, at least a first laser beam having a first wavelength which is absorbed by a gas to be detected or a second laser beam having a second wavelength which is not absorbed by the gas to be detected;

first control means for switching the drive current having a predetermined value corresponding to the first or the second wavelength at a predetermined period, and for supplying the drive current to said tunable wavelength single mode semiconductor laser, said first control means including means for controlling the drive current having the predetermined value corresponding to the first or the second wavelength so that the first and the second laser beams are alternately output from said tunable wavelength single mode semiconductor laser with substantially the same power while the first and the second wavelengths are maintained;

first light-receiving means for receiving first and second response light components generated when the first and the second laser beams emitted alternately from said tunable wavelength single mode semiconductor laser are incident on the object to be detected through the first optical path, and for outputting electrical signals corresponding to received light amounts of the first and the second response light components;

signal processing means for receiving the electrical signals from said first light-receiving means, and for processing a presence/absence condition of gas detection in accordance with a difference between the received light amounts of the first and the second response light components;

second light-receiving means for receiving the first and the second laser beams emitted from said tunable wavelength single mode semiconductor laser through the second optical path, and for outputting detection signals corresponding to the wavelengths and powers of the received first and second laser beams, said second light-receiving means including a wavelength divider for selecting said first laser beam, a first light-receiving element for receiving a beam output from the wavelength divider, and a second light-receiving element for receiving the first and the second laser beams non-selectively; and second control means for feeding back a correction signal for correcting the drive currents having the predetermined values to said first control means in accordance with the detection signal from said second light-receiving means.

2. An apparatus according to claim 1, wherein the response light components comprise light reflected by a portion around the object to be detected.

3. An apparatus according to claim 1, wherein the response light components comprise light transmitted through the object to be detected.

4. An apparatus according to claim 1, wherein said tunable wavelength single mode semiconductor laser comprises a 3-electrode Distributed Bragg Reflector (DFB) laser having first, second and third electrodes, and said first control means includes means for flowing a sum $I_2$ of currents to be flowed to said first and said third electrodes, and for flowing a current $I_1$ to said second electrode, thereby controlling $I_1/(I_1+I_2)$ to be a desired value.

5. An apparatus according to claim 4, wherein, when said second light-receiving element receives the first laser beam, said second control means controls a value (n) of $I_1/(I_1+I_2)$ so that the output from the first light-receiving element takes a maximum value, holds the value (n), and controls $(I_1+I_2)$ so that the output from the first light-receiving element assumes a most desirable value.

6. An apparatus according to claim 4, wherein, when said second light-receiving element receives the first laser beam, said second control means controls a value (n) of $I_1/(I_1+I_2)$ so that the output from the first light-receiving element takes a minimum value, holds the value (n), and controls $(I_1+I_2)$ so that the output from the first light-receiving element assumes a most desirable value.

7. An apparatus according to claim 5, wherein, when said first light-receiving element receives the first laser beam, said second control means scans the value (n) at predetermined intervals, and calculates the most desirable value (n) on the basis of values found by the scan.

8. An apparatus according to claim 6, wherein, when said first light-receiving element receives the first laser beam, said second control means scans the value (n) at predetermined intervals, and calculates the most desirable value (n) on the basis of values found by the scan.

9. An apparatus according to claim 3, wherein said apparatus further comprises:

a first optical fiber for guiding the first and the second laser beams to locations for measurement;

a first lens for emitting the guided laser beams to a space;

a second lens for collecting the laser beams emitted to the space and passed through the gas to be detected; and a second optical fiber for guiding the collected laser beams to said first light-receiving means.

10. A method for detecting a gas, said method comprising the steps of:

providing light source means including a tunable wavelength single mode semiconductor laser, said tunable wavelength single mode semiconductor laser outputting a single mode laser beam having a wavelength tuned in accordance with a drive current to a first optical path and a second optical path, the semiconductor laser emitting, for an objected to be detected, at least a first laser beam having a first wavelength which is absorbed by a gas to be detected or a second laser beam having a second wavelength which is not absorbed by the gas to be detected;

switching the drive current having a predetermined value corresponding to the first or the second wavelength at a predetermined period and supplying the drive current to said tunable wavelength single mode semiconductor laser by first control means, and controlling the drive current having the predetermined value corresponding to the first or the second wavelength so that the first and second laser beams are alternately output from said tunable wavelength single mode semiconductor laser with substantially the same power while the first and the second wavelengths are maintained;

receiving the first and the second laser beams emitted from the tunable wavelength single mode semiconductor laser through the second optical path by first light-receiving means, and outputting detection signals corresponding to the wavelengths and powers of the received first and second laser beams;

feeding back a correction signal for correcting the drive currents having the predetermined values to the first control means by second control means in accordance with the detection signal from the first light-receiving means;

receiving first and second response light components generated when the first and the second laser beams emitted alternately from the tunable wavelength single mode semiconductor laser are incident on the object to be detected through the first optical path by second light-receiving means, and outputting electrical signals corresponding to received light amounts of the first and the second response light components; and receiving the electrical signals from the second light-receiving means by signal processing means, and processing a presence/absence condition of gas detection in accordance with a difference between the received light amounts of the first and the second response light components.

11. A gas detection apparatus, comprising:

light source means including a tunable wavelength single mode semiconductor laser, said tunable wavelength single mode semiconductor laser including means for outputting a single mode laser beam having a wavelength tuned in accordance with a drive current and emitting, for an object to be detected, at least a first laser beam having a first wavelength which is absorbed by a gas to be detected or a second laser beam having a second wavelength which is not absorbed by the gas to be detected;

control means for switching the drive current having a predetermined value corresponding to the first or the second wavelength at a predetermined period, and for supplying the drive current to said tunable wavelength single mode semiconductor laser, said control means including means for controlling the drive current having the predetermined value corresponding to the first or the second wavelength so that the first and the second laser beams are alternately output from said tunable wavelength single mode semiconductor laser with substantially the same power while the first and the second wavelengths are maintained;

light-receiving means for receiving first and second response light components generated when the first and the second laser beams emitted alternately from said tunable wavelength single mode semiconductor laser are incident on the object to be detected, and for outputting electrical signals corresponding to received light amounts of the first and the second response light components wherein the first and the second response light components are transmitted through the object to be detected;

signal processing means for receiving the electrical signals from said light-receiving means, and for processing a presence/absence condition of gas detection in accordance with a difference between the received light amounts of the first and the second response light components;

transmitting means for storing at least said light source means; and receiving means for storing at least said light-receiving means;

wherein said transmitting means and said receiving means include means for performing data communication using the second wavelength between one another.

* * * * *